(12) United States Patent
Eguchi

(10) Patent No.: US 8,786,257 B2
(45) Date of Patent: Jul. 22, 2014

(54) RADIOGRAPHIC IMAGE DETECTION DEVICE AND RADIOGRAPHIC IMAGE CAPTURING SYSTEM

(75) Inventor: Yoshihiko Eguchi, Tokorozawa (JP)

(73) Assignee: Konica Minolta Medical & Graphic, Inc. (JP)

( * ) Notice: Subject to any disclaimer, the term of this patent is extended or adjusted under 35 U.S.C. 154(b) by 323 days.

(21) Appl. No.: 13/389,341

(22) PCT Filed: Feb. 12, 2010

(86) PCT No.: PCT/JP2010/052046
§ 371 (c)(1),
(2), (4) Date: Feb. 7, 2012

(87) PCT Pub. No.: WO2011/021404
PCT Pub. Date: Feb. 24, 2011

(65) Prior Publication Data
US 2012/0133339 A1    May 31, 2012

(30) Foreign Application Priority Data

Aug. 20, 2009  (JP) ................................ 2009-190892

(51) Int. Cl.
*H02J 7/00* (2006.01)
(52) U.S. Cl.
USPC ............................ 320/128; 320/127; 320/132
(58) Field of Classification Search
CPC ...................................................... Y02E 60/12
USPC ........................................................ 320/128
See application file for complete search history.

(56) References Cited

FOREIGN PATENT DOCUMENTS

| JP | 06-342099 A | 12/1994 |
| JP | 2001-224579 A | 8/2001 |
| JP | 2010-046203 A | 3/2010 |
| WO | 2006/080377 | 8/2006 |

OTHER PUBLICATIONS

International Search Report for International application No. PCT/JP2010/052046 mailing date of May 18, 2010 with English Translation.

*Primary Examiner* — Edward Tso
*Assistant Examiner* — Ahmed Omar
(74) *Attorney, Agent, or Firm* — Cantor Colburn LLP

(57) ABSTRACT

A radiographic image capturing system having, a low-current electric power feeding section, a high-current electric power feeding section, and a cassette-type radiographic image detection device having a battery which feeds electric power, the radiographic image detection device including: a power receiving side connection section receiving electric power from an electric power feeding section having been connected; a first charging path converting electric power fed from the power feeding section into charging electric power which is fed to the battery; a second charging path feeding the electric power to the battery without the conversion; and a charging path switching section switching when the low-current electric power feeding section has been connected to the power receiving side connection section, electric power is fed via the first charging path and when the high-current electric power feeding section has been connected, electric power is fed via the second charging path.

9 Claims, 5 Drawing Sheets

RADIOGRAPHIC IMAGE DETECTION DEVICE AND RADIOGRAPHIC IMAGE CAPTURING SYSTEM

CROSS REFERENCE TO RELATED APPLICATIONS

This is a U.S. national stage of application No. PCT/JP2010/052046, filed on Feb. 12, 2010. Priority under 35 U.S.C. §119(a) and 35 U.S.C. §365(b) is claimed from Japanese Application No. 2009-190892, filed Aug. 20, 2009, the disclosure of which is also incorporated herein by reference.

TECHNICAL FIELD

The present invention relates to a radiographic image detection device and a radiographic image capturing system.

BACKGROUND

Conventionally, radiographic image detection devices, in which as a member to acquire a medical radiographic image, a solid-state imaging element referred to as a so-called flat panel detector (FPD) is two-dimensionally arranged, have been known. It is known that such radiographic image detection devices include direct-type devices in which using a photoconductive material such as a-Se (amorphous selenium) as a radiation detection element, radiation energy is directly converted into a charge and then this charge is read out as an electric signal in a pixel unit by a switching element for signal readout such as a two-dimensionally arranged TFT (Thin Film Transistor); and indirect-type devices in which radiation energy is converted into light using a scintillator and then this light is converted into a charge by a photoelectric conversion element such as a two-dimensionally arranged photodiode to be read out as an electric signal using a TFT.

And, over recent years, cassette-type radiographic image detection devices configured to be drivable with no cable and portable in which a battery is incorporated in the interior have been developed (for example, refer to Patent Document 1 and Patent Document 2). In the case where such a configuration is made for a radiographic image detection device, image capturing with a high degree of freedom including portable image capturing on the bed side of the patient can be carried out.

Conventionally, as a type in which a battery is charged, there has been used a type in which on the charging path, a charging circuit is provided and electric power having been fed from the outside is converted into electric power for battery charging to charge a battery (a first type); or a type in which electric power for battery charging is directly fed from the outside to charge a battery (a second type).

In the case of the first type, when electric power is fed from the outside, the voltage of the fed electric power is allowed to be high and the current value thereof is allowed to be low, and thereby conversion into appropriate voltage and current for a battery to be charged in the charging circuit of the interior can be carried out. In the case of employing this method, the current value needs not to be increased, and thereby when charging is carried out using a power feeding cable, the diameter of the power feeding cable needs not to be increased. Thereby, the power feeding cable does not stand in the way of image capturing even with charging, resulting in excellent manageability and operability.

On the other hand, in the case of the second type, since no power conversion is carried out inside a radiographic image detection device, just a small loss results, and thereby heat generation in the device interior can be inhibited. Further, quick charging with high current can be carried out.

PRIOR ART DOCUMENTS

Patent Documents

Patent Document 1: Unexamined Japanese Patent Application Publication No. 2001-224579
Patent Document 2: Unexamined Japanese Patent Application Publication No. 6-342099

BRIEF DESCRIPTION OF THE INVENTION

Problems to be Solved by the Invention

However, in the case of employing the first type, the efficiency of a charging circuit is considered to be 80-90%, and therefore, when power feeding is carried out at constant voltage (for example, 15 V) from the outside to charge a 3.6 V/4 A battery, a maximum loss of 2.88 W (i.e., 3.6 V×4 A×(1−0.8)) is produced and then this loss amount is generated as heat in the interior of the device. Thereby, a sensor panel section susceptible to the influence of heat and a signal value of a signal readout circuit become unstable, resulting in adverse effects on image quality.

On the other hand, in the case of the second type, since no power conversion is carried out in the interior, charging current of the same current value flows from an external power supply to the battery. Therefor, the current ratings of a power feeding cable and a connector section have to be increased. Especially when image capturing is intended to be carried out with connection to a power feeding cable, the power feeding cable lies in the way, resulting in poor operability. Further, in the case of this type, voltage and current need to be adjusted via feedback. As the length of the power feeding cable is increased, the inductance of the power feeding cable is included, resulting in the difficulty of feedback control to carry out control voltage/current via monitoring. Thereby, there is noted the problem that the power feeding cable has to be thick and short.

In this manner, in both the first type and the second type to charge a battery, there are merits and demerits. To make use of the advantage of a cassette-type radiographic image detection device in which image capturing of a high degree of freedom can be carried out, charging in which merits of both types are utilized is desirably performed.

Thus, in view of the above circumstances, the present invention was completed. An object thereof is to provide a radiographic image detection device and a radiographic image capturing system, in which in the case where charging is merely carried out or charging and image capturing are carried out with closest connection to an external power supply, quick charging with high current can be carried out, and also in the case of image capturing, excellent manageability is expressed and no image quality is degraded.

Means to Solve the Problems

To solve the above problems, the radiographic image capturing system of the present invention having, a low-current electric power feeding section to feed low-current electric power, a high-current electric power feeding section to feed high-current electric power, and a cassette-type radiographic image detection device in which a battery to feed electric power to each functional section is incorporated in a housing so as to drive the each functional section by feeding electric power from the battery, the radiographic image detection device comprising:

a power receiving side connection section which is configured to be electrically connectable to the low-current electric power feeding section and the high-current electric power feeding section to receive electric power from an electric power feeding section having been connected, a first charging path in which a power conversion section to convert electric power fed from the electric power feeding section into charging electric power is provided and electric power fed from the electric power feeding section is fed to the battery after converted into charging electric power by the power conversion section, a second charging path in which electric power fed from the electric power feeding section is fed to the battery without conversion, an electric power feeding section determination section to determine whether an electric power feeding section currently connected to the power receiving side connection section is the low-current electric power feeding section or the high-current electric power feeding section, and a charging path switching section in which the first charging path and the second charging path are switched so that when the electric power feeding section determination section has determined that the low-current electric power feeding section has been connected to the power receiving side connection section, electric power is fed via the first charging path and when the electric power feeding section determination section has determined that the high-current electric power feeding section has been connected to the power receiving side connection section, electric power is fed via the second charging path.

To solve the above problems, the radiographic image detection device of a cassette-type incorporating a battery to feed electric power to each functional section in a housing so as to drive the each functional section by feeding electric power from the battery, the radiographic image detection device comprising:

a power receiving side connection section which is configured to be electrically connectable to an external low-current electric power feeding section to feed low-current electric power and an external high-current electric power feeding section to feed high-current electric power so as to receive electric power from an outside, a first charging path in which a power conversion section to convert electric power fed from an outside into charging electric power is provided and electric power fed from the outside is fed to the battery after converted into charging electric power by the power conversion section, a second charging path in which electric power fed from the outside is fed to the battery without conversion, an electric power feeding section determination section to determine whether an electric power feeding section connected to the power receiving side connection section is the low-current electric power feeding section or the high-current electric power feeding section, and a charging path switching section in which the first charging path and the second charging path are switched so that when the electric power feeding section determination section has determined that the low-current electric power feeding section has been connected to the power receiving side connection section, electric power is fed via the first charging path and when the electric power feeding section determination section has determined that the high-current electric power feeding section has been connected to the power receiving side connection section, electric power is fed via the second charging path are provided.

Effects of the Invention

According to this invention, during connection to a low-current electric power feeding section such as a power feeding cable, charging current is allowed to decrease, and thereby the current capacity of the power feeding cable can be reduced. Thereby, the power feeding cable can be thinner, and then when image capturing is concurrently carried out with charging, the manageability of a radiographic image detection device is increased.

Further, since the current value fed from the outside during connection to a low-current electric power feeding section can be reduced, only a small loss in the charging circuit is produced, resulting in inhibiting heat generation. Thereby, adverse effects on a sensor panel section susceptible to the influence of heat and a signal readout circuit are minimized and then image quality degradation can be inhibited.

Still further, when a high-current electric power feeding section has been connected, the effect that charging can be carried out with high current and thereby quick charging in a short period of time can be carried out is produced.

PREFERRED EMBODIMENT OF THE INVENTION

Figure 1:
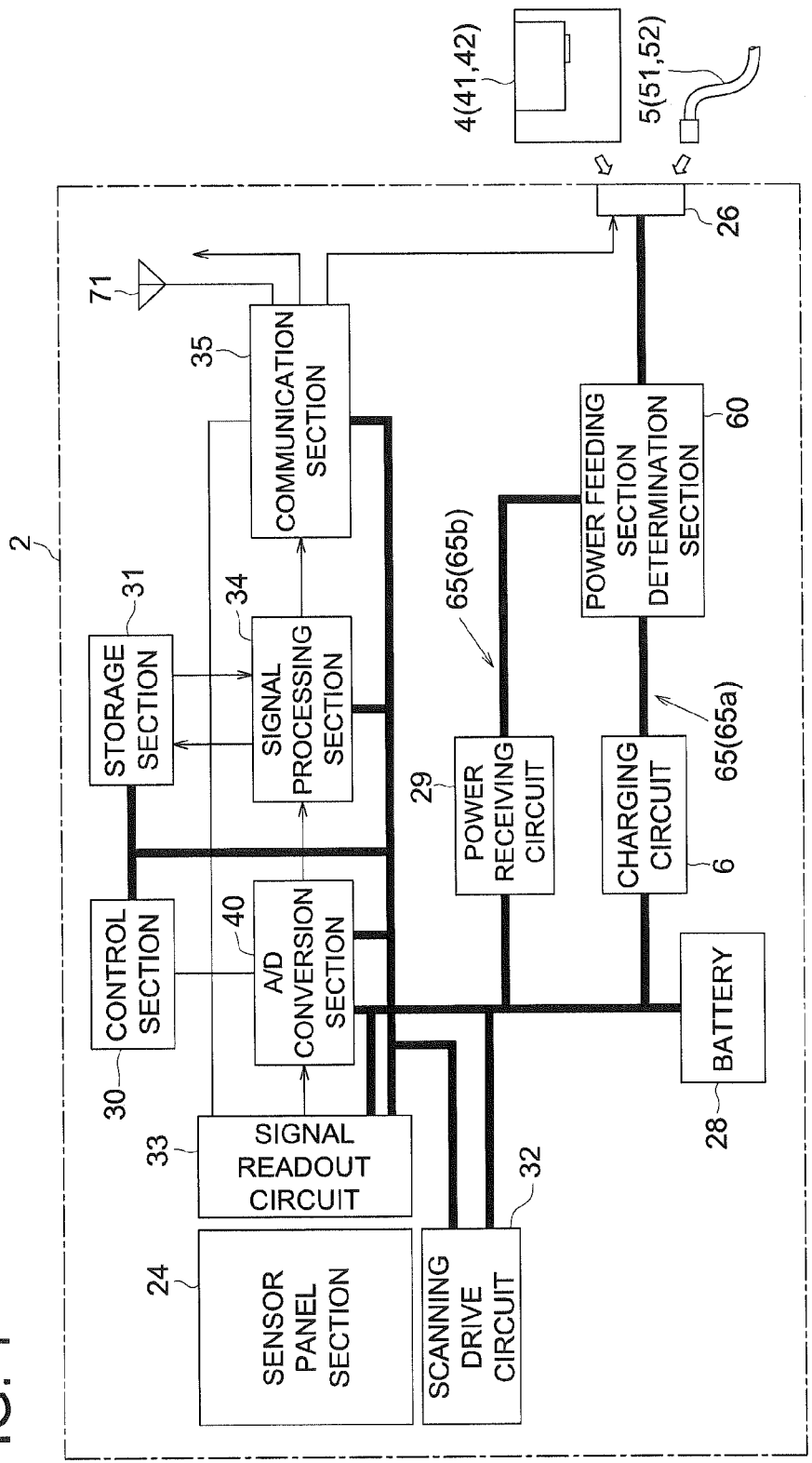
FIG. 1 is a schematic view showing the functional constitution of a radiographic image detection device according to a present embodiment

With reference to FIG. 1-FIG. 5, a preferred embodiment of a radiographic image detection device according to the present invention will now be described that by no means limits any embodiment to which the present invention is applicable.

In the present embodiment, a radiographic image detection device 2 is a portable cassette-type FPD in which a so-called flat panel detector (hereinafter, referred to also as "FPD") is configured into a cassette-type, being used for radiographic image capturing to acquire radiographic image data (hereinafter, referred to simply as "image data").

Incidentally, in the following description, as the radiographic image detection device 2, a so-called indirect-type radiographic image detection device, in which a scintillator is provided and then emitted radiation is converted into electromagnetic radiation having another wavelength such as visible light to acquire an electric signal, will be described. However, the present invention is also applicable to a so-called direct-type radiographic image detection device in which via no scintillator, radiation is directly detected using a radiation detection element.

Herein, the radiographic image detection device 2 of the present embodiment incorporates a battery 28 as described later, having 2 types of charging path, as a charging path 65 (refer to FIG. 4) to charge this battery 28, including a first charging path 65a to convert electric power having been fed from the outside into electric power for battery charging to be fed to the battery 28 and a second charging path 65b to directly feed electric power having been fed from the outside to the battery 28.

In the radiographic image detection device 2, either of 2 drive states including the battery drive state in which electric power is acquired only from the battery 28 to drive each functional section and the external power feeding drive state in which via an electric power feeding section such as a power feeding cable 52, power feeding is carried out from the outside for driving can be selected. In the case of this external power feeding drive state, a constitution is made so as to charge the battery 28 simultaneously with the drive of each functional section.

The electric power feeding section connected to the radiographic image detection device 2 according to the present embodiment includes an electric power feeding section 5 which is a low-current electric power feeding section to feed low-current electric power serving as a dual-purpose electric power feeding section to concurrently drive each functional section and charge the battery 28 and a cradle 4 which is a high-current electric power feeding section to feed high-current electric power serving as a charging-dedicated electric power feeding section dedicated to charging the battery 28. The electric power feeding section 5 is provided with an AC/DC power supply 51 and a power feeding cable 52. The cradle 4 is provided with an AC/DC power supply 41 and an output connector section 42 functioning as a cradle connection terminal.

Figure 4:
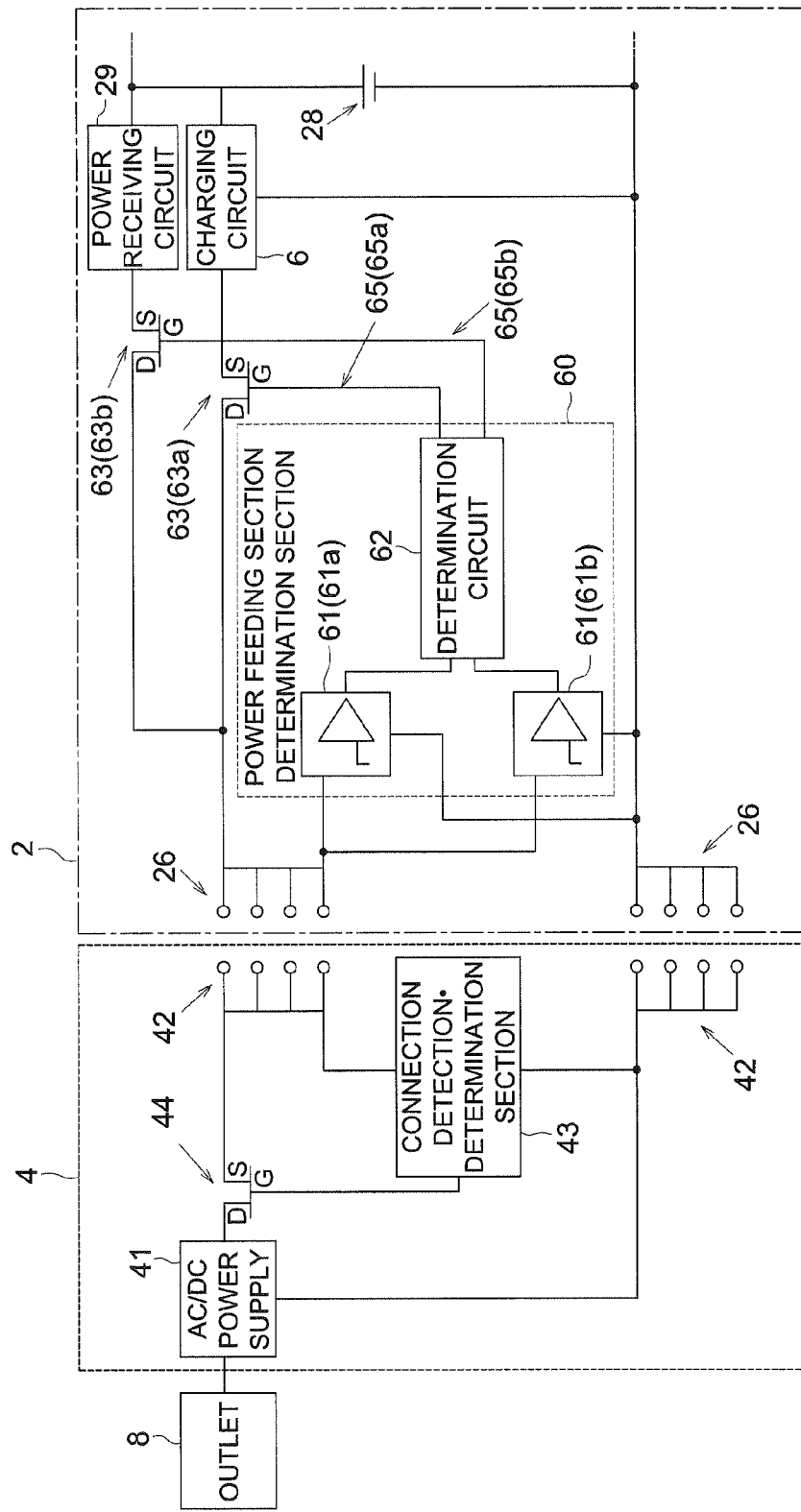
FIG. 4 is a main part block diagram showing the schematic constitution of the charging path in the present embodiment.

The cradle 4 is configured to be able to feed electric power to the radiographic image detection device 2 from the outside by mounting the radiographic image detection device 2 therein, being provided with an AC/DC power supply 41 connected with an outlet 8 connected to an unshown external power supply (a commercial power supply) and an output connector section 42 to output electric power fed from the AC/DC power supply 41 to the outside (refer to FIG. 4). From the cradle 4, electric power is fed via the output connector section 42 and the detection device side connector section 26. The AC/DC power supply 41 always outputs electric power at constant voltage independently of load variation. The output connector section 42 feeds electric power to the radiographic image detection device 2 at this given voltage.

Further, the cradle 4 is provided with a connection detection-determination section 43 to detect/determine whether the output connector section 42 has been connected to the detection device side connector section 26 of the radiographic image detection device 2 and a switch 44 to switch whether electric power is output to the outside (refer to FIG. 4). The method in which the connection detection-determination section 43 detects/determines the connection of the output connector section 42 and the detection device side connector section 26 is not specifically limited. For example, physical contact to the output connector section 42 may be detected.

Further, as the type of the switch 44, an FET (Field-Effect Transistor) is generally used with no limitation thereto. A constitution using, for example, any of an electromagnetic switch (electromagnetic relay), a semiconductor switch (SSR), and a photoelectric relay (photorelay) may be made. For example, in the case where the switch 44 is constituted using an FET, when the connection detection-determination section 43 detects that the output connector section 42 and the detection device side connector section 26 have been connected to each other and then a given ON voltage has been applied to the gate (represented by "G" in FIG. 4) of the switch 44, the switch 44 is turned on and then current flows from the drain (represented by "D" in FIG. 4) to the source (represented by "S" in FIG. 4).

In the present embodiment, when the radiographic image detection device 2 is mounted in the cradle 4, the output connector section 42 of the cradle 4 side is electrically connected to the detection device side connector section 26 of the radiographic image detection device 2, and then via the AC/DC power supply 41, electric power (for example, charging current of a high current value of 10 A) to directly (namely, with no power conversion) charge the battery 28 is fed to the radiographic image detection device 2 from an external power supply.

The electric power feeding section 5 is connected to the radiographic image detection device 2 so as to feed electric power to the radiographic image detection device 2 from the outside. One end side of the power feeding cable 52 of the electric power feeding section 5 is connected to the detection device side connector section 26 of the radiographic image detection device 2 and the other end side thereof is connected to the AC/DC power supply 51. In the same manner as the AC/DC power supply 41, the AC/DC power supply 51 always outputs electric power at constant voltage independently of load variation. The AC/DC power supply 51 is connected to an external power supply (a commercial power supply) via an outlet (not shown). Thereby, when one end side of the power feeding cable 52 is connected to the detection device side connector section 26 of the radiographic image detection device 2, electric power is fed to the radiographic image detection device 2 from the external power source. In this case, the electric power of the external power supply fed via an outlet is converted by the AC/DC power supply 51. The electric power fed via the power feeding cable 52 after conversion has high voltage and small current value. As described later, electric power having been fed via the power feeding cable 52 is converted into voltage and current suitable for the battery 28 to be charged in the charging circuit 6 inside the radiographic image detection device 2.

Herein, between the power feeding cable 52 and the external power supply, in the same manner as in the cradle 4, a connection detection-determination section to detect/determine whether the power feeding cable 52 has been connected to the detection device side connector section 26 of the radiographic image detection device 2 and a switch 44 to switch whether electric power is output to the outside (the radiographic image detection device side) (both are not shown) are provided. Incidentally, the constitution of the connection detection-determination section and the switch is the same as one provided for the cradle 4 and therefore description thereof will be omitted.

Herein, in the present embodiment, one example, in which the electric power feeding section 5 is provided with an AC/DC power supply 51 and the power feeding cable 52 is connected to the AC/DC power supply 51 to feed electric power to the radiographic image detection device 2 from an external power supply, has been described. However, the method to connect the power feeding cable 52 and the external power supply together is not limited thereto. For example, the constitution of connection to an external power supply via a cradle 4 (and an AC/DC power supply 41) is employable. In this case, inside the cradle 4, a functional section to detect/determine whether the detection device side connector section 26 of the radiographic image detection device 2 is connected to the output connector section 42 of the cradle 4 is provided.

Incidentally, the diameter of a power feeding cable 52 is not specifically limited. However, in the present embodiment, it is assumed that image capturing is carried out with connection to the power feeding cable 52 and therefore it is preferable that the power feeding cable 52 have small diameter with excellent manageability as much as possible. When the diameter of the power feeding cable 52 is small, feedable current capacity decreases. However, at that rate, the power loss corresponding to the amount of the voltage decrease in the power feeding cable 52 can be allowed to decrease. Further, as feedable current capacity decreases, at that rate, heat generation in a charging circuit 6 to be described later also decreases, and thereby image quality degradation due to the influence of heat can be inhibited. Still further, the generation amount of noise produced from the charging circuit 6 can also be inhibited.

Figure 2:
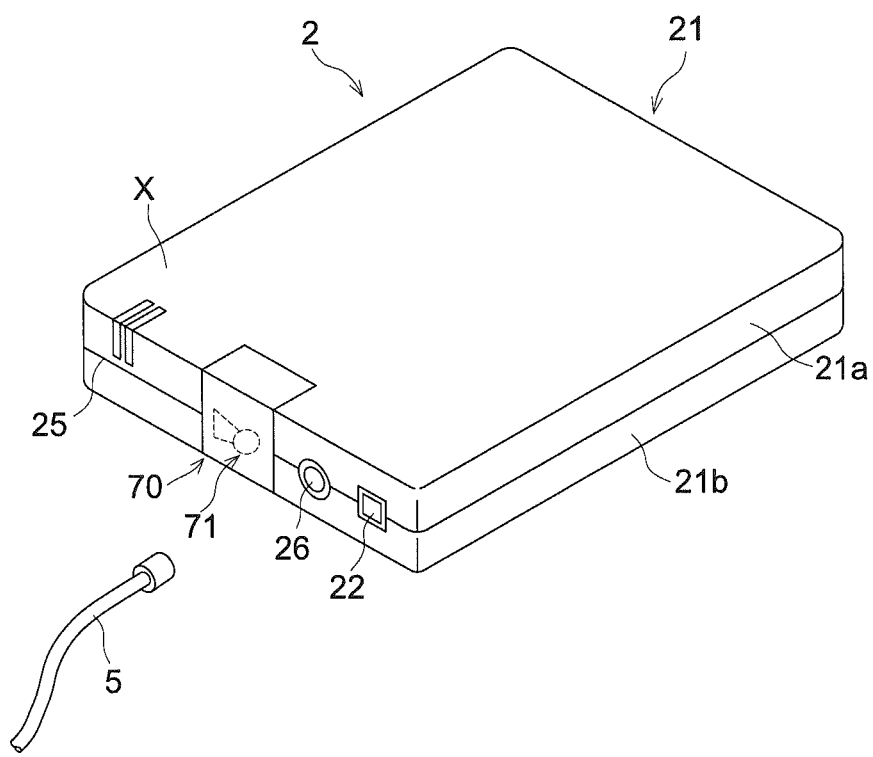
FIG. 2 is a perspective view showing the exterior appearance of the radiographic image detection device shown in FIG. 1.

FIG. 2 is a perspective view of the radiographic image detection device 2 in the present embodiment. As shown in FIG. 2, the radiographic image detection device 2 is provided with a housing 21 for inner protection. In the housing 21, at least the face X of the side where radiation is irradiated (hereinafter, referred to as the radiation entering face X) is formed with a material such as a carbon plate or a plastic material through which radiation passes. Herein, FIG. 2 shows a case in which the housing 21 is formed with a front member 21a and a back member 21b, but the shape and configuration are not specifically limited. Other than this, the housing 21 can be formed into a cylindrical, so-called monocoque shape.

As shown in FIG. 2, in the present embodiment, in the side portion of the radiographic image detection device 2, a power switch 22, an indicator 25, and a detection device side connector section 26 are arranged.

The power switch 22 switches the ON/OFF of the power supply of the radiographic image detection device 2. When the power switch 22 is operated, a signal to instruct the initiation and disconnection of power feeding to each functional section of the radiographic image detection device 2 by a battery 28 (refer to FIG. 1) to be described later is output to a control section 30 (refer to FIG. 1) to be described later. When the radiographic image detection device 2 is not used for image capturing, the power supply is allowed to remain off (namely, power feeding to each functional section by the battery 28 is disconnected) and thereby the power consumption of the battery 28 can be controlled.

The indicator 25 is constituted of, for example, an LED to display the remaining charge level of the battery 28 and various kinds of operational situation.

Further, the radiographic image detection device 2 is provided with a battery 28 to feed electric power to each functional section thereof.

The battery 28 can be charged, and a chargeable secondary battery such as, for example, a nickel-cadmium battery, a nickel-hydrogen battery, a lithium-ion battery, a small sealed lead battery, or a lead storage battery or a storage element such as an electric double layer capacitor or a lithium-ion capacitor (LIC) is applicable.

Of these, a lithium-ion capacitor is specifically preferable since excellent storage efficiency is expressed and also quick charging can be carried out with high current (for example, 5-10 A), resulting in a significant decrease in charging time.

Further, in the side portion of the radiographic image detection device 2, a lid member 70 to be opened and closed for replacement of a battery 28 incorporated in the housing 21 is provided. In the side portion of the lid member 70, an antenna device 71, in which the radiographic image detection device 2 carried out wireless information transmission to and reception from the outside via a wireless access point 113 (refer to FIG. 5) to be described later, is embedded.

The detection devise side connector section 26 is configured so as to be able to be electrically connectable to each of the output connector section 42 of the cradle 4 and the power feeding cable 52, and is a power receiving side connection section to receive electric power fed to the radiographic image detection device 2 from the outside.

As described later, when the output connector section 42 of the cradle 4 is connected to the detection device side connector section 26, high current is fed to the battery 28 so as to carry out quick charging. Further, a constitution is made in which when the power feeding cable 52 of the electric power feeding section 5 is connected to the detection device side connector section 26, the battery 28 can be charged as each functional section is driven by electric power fed from the outside.

Inside the radiation entering face X of the housing 21 (refer to FIG. 2), an unshown scintillator layer to absorb radiation having entered from the radiation entering face X to be converted into light of a wavelength containing visible light is formed. For the scintillator layer, those formed using a phosphor in which a luminescent center material is activated in a host body such as, for example, CsI:Tl, $Gd_2O_2S$:Tb or ZnS:Ag are usable.

On the face side opposite to the face of the side where radiation of the scintillator layer enters, there is provided a sensor panel section 24 serving as a detection section in which a plurality of photoelectric conversion elements 223 (refer to FIG. 3) to convert light having been output from the scintillator layer into an electric signal is plurally arranged in a two-dimensional manner. The photoelectric conversion element 23 is, for example, a photodiode and constitutes, with a scintillator layer, a radiographic detection element to convert radiation having passed through the subject into an electric signal.

In the present embodiment, a reading section 45 (refer to FIG. 3) serving as a reading section to read an output value of each photoelectric conversion element 23 of this sensor panel section 24 via a control section 30, a scanning drive circuit 32, and a signal readout circuit 33 is constituted.

Figure 3:
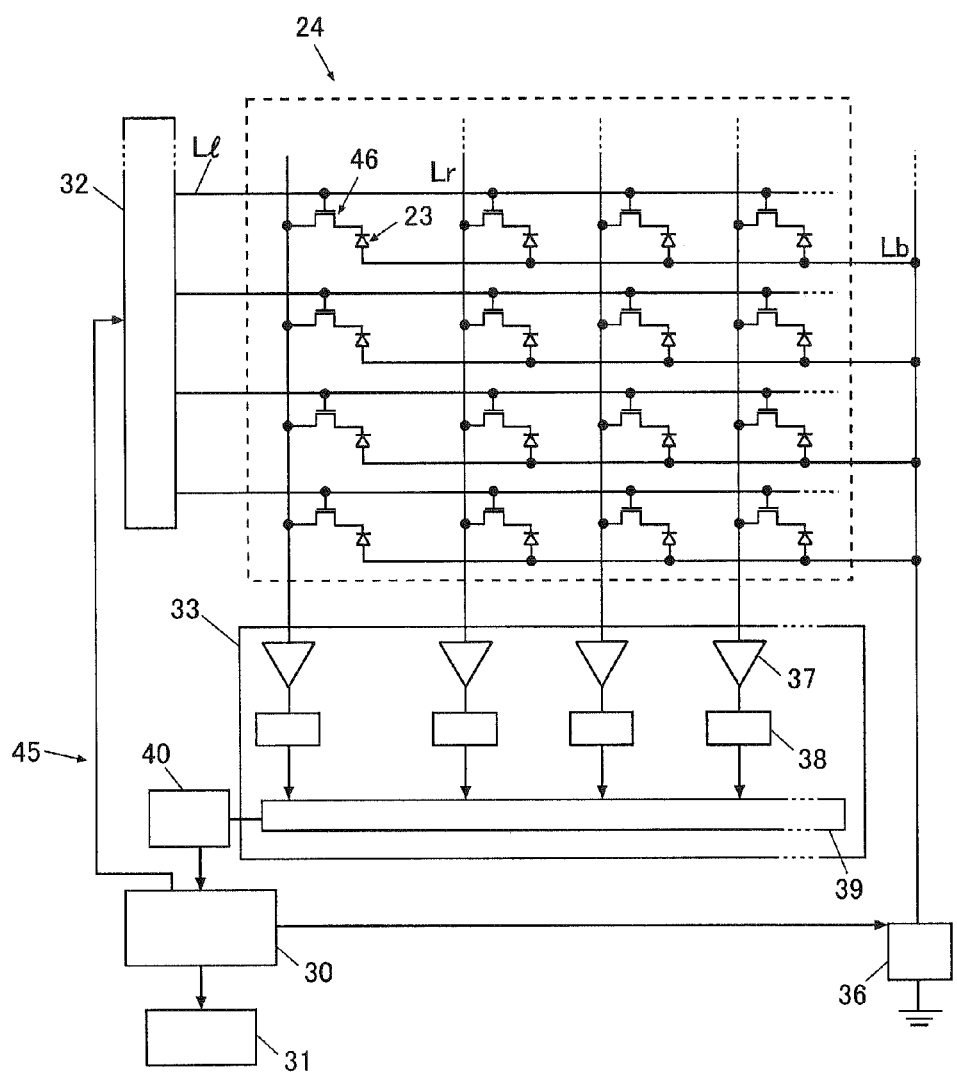
FIG. 3 is an equivalent circuit diagram showing the constitution of the sensor panel section and the reading section of the radiographic image detection device shown in FIG. 1.

The constitution of the sensor panel section 24 and the reading section 45 will further be described with reference to the equivalent circuit diagram of FIG. 3. As shown in FIG. 3, one electrode of each photoelectric conversion element 23 of the sensor panel section 24 is each connected to the source electrode of a TFT 46 as a switching element for signal readout. Further, the other electrode of each photoelectric conversion element 23 is connected to a bias line Lb. The bias line Lb is connected to a bias power supply 36 to apply a reverse bias voltage to each photoelectric conversion element 23 from the bias power supply 36.

The gate electrode of each TFT 46 is connected to a scanning line Ll extending from the each scanning drive circuit 32. The gate electrode of the TFT 46 is applied with a readout voltage (ON voltage) or OFF voltage from an unshown TFT power supply via this scanning line Ll. Further, the drain electrode of each TFT 46 is each connected to a signal line Lr. Each signal line Lr is each connected to an amplifier circuit 37 in each signal readout circuit 33, and the output line of each amplifier circuit 37 is connected to an analog multiplexer 39 via each sample-hold circuit 38. Further, the signal readout circuit 33 is connected to an A/D conversion section 40 as the processing section to convert a signal into a digital signal. An analog image signal having been transmitted from the analog multiplexer 39 is converted into a digital image signal by the A/D conversion section 40. The signal readout circuit 33 is connected to the control section 30 via this A/D conversion section 40 to output such a digital image signal to the control section 30. A storage section 31 is connected to the control section 30 to a storage section 31. The control section 30 stores the digital image signal having been transmitted from the A/D conversion section 40 as image data in the storage section 31.

The control section 30 is a computer provided with an unshown CPU (Central Processing Unit), ROM (Read Only Memory), and RAM (Random Access Memory) and totally controls the entire radiographic image detection device 2.

The signal processing section 34 is a functional section to carry out a predetermined signal processing for image data to allow the data to be one having a format suitable for outputting the image data to the outside.

In the ROM, programs to carry out various kinds of processing in the radiographic image detection device 2 such as photographed image data generation processing, offset correction value generation processing, and power feeding control processing, as well as various kinds of control program and parameters are stored.

The control section 30 reads out a predetermined program stored in the ROM to be developed on the work area of the RAM and allows the CPU to execute various kinds of processing based on the program.

The storage section 31 incorporates, for example, a HDD (Hard Disk Drive) or a flash memory. In the storage section 31, photographed image data generated by the reading section 45 (refer to FIG. 3) (image data based on radiation passed through the subject) and dark read values (image data acquired without radiation irradiation) are stored. Herein, the storage section 31 may be a built-in memory or a removable memory such as a memory card. Further, its capacity is not specifically limited but preferably has a capacity capable of storing image data for a plurality of sheets. When such a storage section is provided, it becomes possible that the subject is continuously irradiated with radiation and at each time, image data is stored and accumulated for continuous image capturing and moving image capturing.

The communication section 35 is connected to the antenna device 71 and performs transmission to and reception from an external device such as a console 101 with respect to various kinds of signal based on the control of the control section 30. The communication section 35 wirelessly communicates with an external device such as a console 101 via a wireless access point 113. In the present embodiment, the communication section 35 transmits image data based on an image signal having been read by the reading section 45, followed by being converted from an analog signal to a digital signal in the A/D conversion section 40 to the console 101 being an external device and also receives image capturing order information from the console 101.

As shown in FIG. 1 and FIG. 4, between the battery 28 and the detection device side connector section 26, an electric power feeding section determination section 60 serving as the electric power feeding section determination section to determine whether either the output connector section 42 of the cradle 4 or the power feeding cable 52 of the electric power feeding section 5 has been connected to the detection device side connector section 26 is provided.

In the cradle 4 and the electric power feeding section 5, different voltages of electric power are set. On the basis of such setting, the electric power feeding section determination section 60 detects the voltage value of electric power fed from the detection device side connector section 26 to detect/determine whether based on the level of this voltage value, either the power feeding cable 52 or the output connector section 42 of the cradle 4 has been connected to the detection device side connector section 26. Herein, the electric power feeding section determination section 60 may measure the current of electric power fed to the detection devise side connector section 26 to detect/determine whether either the power feeding cable 52 or the output connector section 42 of the cradle 4 has been connected to the detection device side connector section 26.

The method of detection/determination using the electric power feeding section determination section 60 is not specifically limited. However, in the present embodiments, the voltage of electric power fed to the detection device side connector section 26 is detected to detect/determine whether the electric power feeding section 5 or the cradle 4 has been connected.

Specifically, as shown in FIG. 4, the electric power feeding section determination section 60 is provided with 2 comparators 61 connected to the detection device side connector section 26 and one determination circuit 62.

In the present embodiment, when the power feeding cable 52 is connected to the detection device side connector section 26 to feed electric power by the electric power feeding section 5, electric power having been fed from the outside is temporarily converted into voltage-current suitable for charging the battery 28 in an inner charging circuit 6 to be fed to the battery 28 and thereby electric power having a high voltage and a low current value (for example, voltage: 15 V, current value: 3 A) is fed. On the other hand, when the cradle 4 is connected to the detection device side connector section 26, electric power having been fed from an external power supply is directly fed to the battery 28 as-fed without power conversion, and thereby electric power having a low voltage and a high current value (for example, voltage: 3.6 V, current value: 10 A) is fed.

Therefor, in one of the comparators 61 (hereinafter, referred to as "a first comparator 61a"), 15 V is set as a reference voltage, and then this reference voltage and the voltage of electric power fed from the detection device side connector section 26 are compared to output an Hi signal if higher than the reference voltage 15 V and to output an Lo signal if lower than that to the determination circuit 62. Further, in the other comparator 61 (hereinafter, referred to as "a second comparator 61b"), 3.6 V is set as a reference voltage, and then this reference voltage and the voltage of electric power fed from the detection device side connector section 26 are compared to output an Hi signal if higher than the reference voltage 3.6 V and to output an Lo signal if lower than that to the determination circuit 62.

On a first charging path 65a and a second charging path 65b each, a switch 63 (a first switch 63a and a second switch 63b) as the charging path switching section to switch the charging path 65 is provided As the type of the switch 63, an FET (Field-Effect Transistor) is generally used but a constitution may be made using any of an electromagnetic switch (electromagnetic relay), a semiconductor switch (SSR), and a photoelectric switch (photorelay).

The determination circuit 62 switches ON/OFF of this switch 63 based on signals having been output from the first comparator 61a and the second comparator 61b.

Namely, the determination circuit 62 determines, based on signals having been output from the first comparator 61a and the second comparator 61b, whether the power feeding cable 52 or the output connector section 42 has been connected to the detection device side connector section 26 or neither thereof has been connected. Then, when the judgment that the power feeding cable 52 has been connected is made, a predetermined ON voltage is applied to the gate of the switch 63 on the first charging path 65a provided with a charging circuit 6 (hereinafter, referred to as "a first switch 63a"). Thereby, the first switch 63a is turned on and then the state where current flows from the drain (represented by "D" in FIG. 4) to the source (represented by "S" in FIG. 4) is created. Further, when the judgment that the cradle 4 has been connected is made, a predetermined ON voltage is applied to the gate of the switch 63 on the second charging path 65b provided with a charging circuit (hereinafter, referred to as "a second switch 63b"). Thereby, the second switch 63b is turned on and then the state where current flows from the drain (represented by "D" in FIG. 4) to the source (represented by "S" in FIG. 4) is created. On the other hand, when the judgment that neither the power feeding cable 52 nor the output connector section 42 has been connected to the detection device side connector section 26 is made, no ON voltage is applied to any of the switch 63 gates. Thereby, blocking is made between the battery 28 and the detection device side connector section 26.

The determination circuit 62 is provided with, for example, a table to coordinate which switch 63 gate an ON voltage is applied to based on the combination of signals having been output from the first comparator 61a and the second comparator 61b. With reference to this table, the determination circuit 62 determines whether an ON voltage is applied.

Incidentally, the method of determination by the determination circuit 62 and the manner of control of the switch 63 are not limited to those exemplified here. For example, the determination circuit 62 may be a logic circuit such as a flip flop operated in response to Hi and Lo signals output from the first comparator 61a and the second comparator 61b based on no control using the table.

Herein, in the present embodiment, the electric power feeding section determination section 60 is configured to detect voltage change using the comparator 61 to determine which has been connected to the detection device side connector section 60, the output connector section 42 or the power feeding cable 52, but the method of determination by the electric power feeding section determination section 60 is not specifically limited. For example, just one comparator 61 may be provided to determine that the output connector section 42 has been connected in the case of being lower than a given reference voltage and to determine that the power feeding cable 52 has been connected in the case of being higher than the reference voltage. Further, a voltmeter to measure voltage may be provided to make a determination based on a value measured by the voltmeter. Still further, the detection device side connector section 26 may be provided with a mechanical switch (not shown) to switch the ON/OFF state of the switch when the cradle 4 has been connected and the power feeding cable 52 has been connected, and further, a detection contact may be provided to change the short circuit/open state of a contact when the cradle 4 has been connected and the power feeding cable 52 has been connected.

On the first charging path, a charging path 6 is provided as a power conversion section to convert electric power having been fed from the outside to electric power to charge the battery 28.

The charging path 6 is provided with, for example, an IC to convert electric power having been fed from the outside to electric power of voltage and current suitable for charging the battery 28 and an inductor to smooth the voltage-current of electric power having been transmitted to the charging circuit, as well as a capacitor and a resistance (any of these is not shown).

On the second charging circuit, a power receiving circuit 29 is provided. The power receiving circuit 29 is provided with a filter (not shown) to cut noise of charging current fed from the outside and then transmitted to the battery 28. Further, to prevent an excessive current flow to the battery 28, a fuse may be provided.

Figure 5:
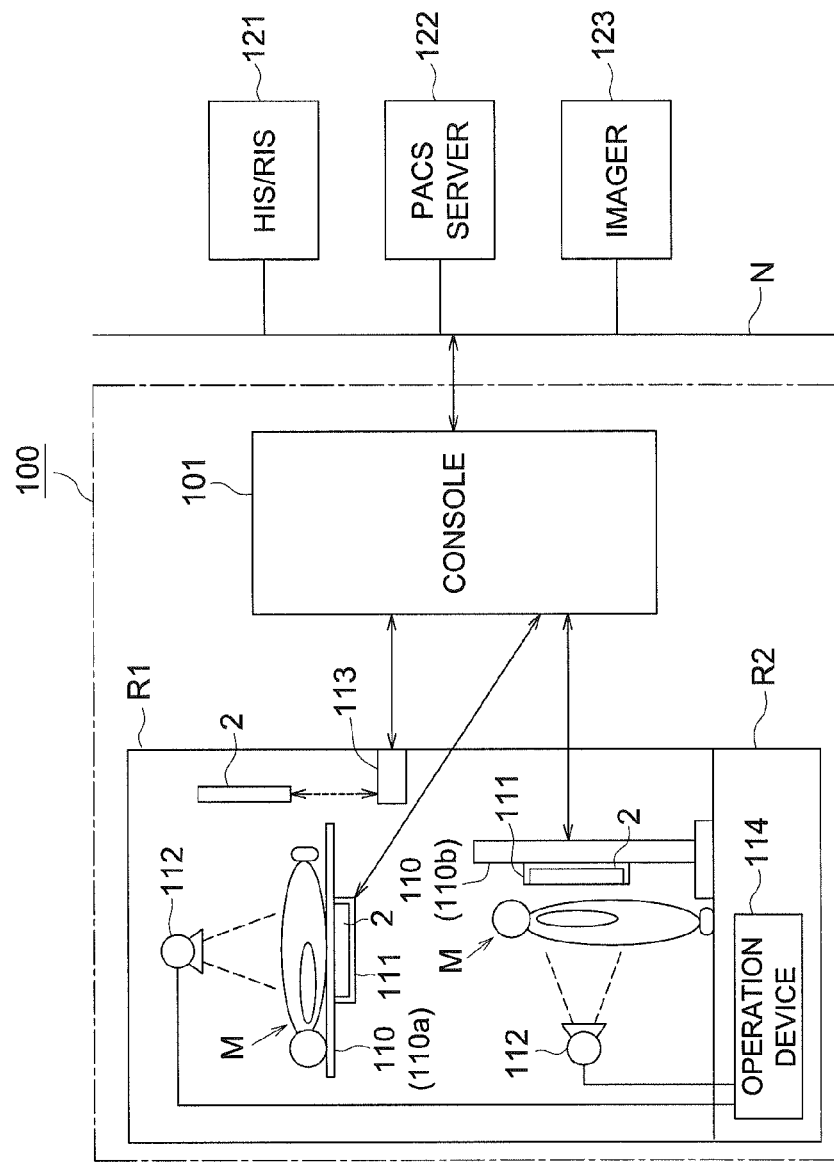
FIG. 5 is a schematic view showing one example of the system constitution of a radiographic image capturing system according to the present embodiment.

Incidentally, this radiographic image detection device 2 is used, for example, by being arranged in a radiographic image capturing system 100 as shown in FIG. 5.

The radiographic image capturing system 100 is provided with, for example, a console 101 communicable with this radiographic image detection device 2.

As shown in FIG. 5, the radiographic image detection device 2 is provided in an image capturing room R1 for image capturing of the subject which is part of patient M (the image capturing site of patient M) via radiation irradiation, and the console 101 is provided corresponding to this image capturing room R1.

Herein, in the present embodiment, there will be described an example in which one image capturing room R1 is provided in the radiographic image capturing system and 3 radiographic image detection devices 2 are arranged in the image capturing room R1. However, the number of image capturing rooms and the number of radiographic image detection devices 2 provided in each image capturing room are not limited to the shown example.

Further, when there are a plurality of image capturing rooms R1, a console 101 needs not to be provided for each image capturing room R1 but just one console 101 may be allowed to respond to the plurality of image capturing rooms R1.

In the image capturing room R1, a radiation generation apparatus 112 is placed provided with a bucky apparatus 110 provided with a cassette holding section 111 in which a radiographic image detection device 2 can be mounted and held and a radiation source (not shown) such as an X-ray tube to irradiate the subject (the image capturing site of patient M) with radiation. The cassette holding section 111 is mounted with the radiographic image detection device 2 during image capturing Incidentally, FIG. 5 exemplifies the case where in an image capturing room R1, each one of a bucky apparatus 110a for spine position image capturing and a bucky apparatus 110b for standing position image capturing is provided. However, the number of the bucky apparatuses 110 placed in the image capturing room R1 is not specifically limited. Further, the present embodiment exemplified a constitution in which one radiation generation apparatus 112 is provided for each bucky apparatus 110. However, it is possible that in the image capturing room R1, just one radiation generation apparatus 112 is provided to be allowed to respond to a plurality of bucky apparatuses 110, and then its position is moved and the radiation irradiation direction is changed appropriately to be used.

Further, the image capturing room R1 is a room to shield radiation and also block radio waves for wireless communications, and therefor in the image capturing room R1, an wireless access point (a base station) 113 is provided to relay communications when a radiographic image detection device 2 and an external device such as a console 101 communicate with each other.

Still further, in the present embodiment, a front room R2 is provided adjacent to the image capturing room R1. In the front room R2, an operation device 114 is arranged in which the radiological technician or the doctor (hereinafter, referred to as "the operator") controls the tube voltage, the tube current, and the irradiation field stop of a radiation generation apparatus 112 to irradiate the subject with radiation and operates a bucky apparatus 110.

Control signals to control radiation irradiation conditions of the radiation generation apparatus 112 are transmitted to the operation device 114 from the console 101. And then, the radiation irradiation conditions of the radiation generation apparatus 112 are set based on the control signals from the console 101 having been transmitted to the operation device 114. The radiation irradiation conditions include, for example, exposure initiation/termination timing, radiation tube current value, radiation tube voltage value, and filter type.

An exposure instruction signal to instruct radiation exposure is transmitted to the radiation generation apparatus 112 from the operation device 114. Then, the radiation generation apparatus 112 irradiates predetermined radiation for a predetermined duration at a predetermined timing based on the exposure instruction signal.

The console 101 is a computer provided with a control section incorporating a CPU (Central Processing Unit), a storage section, an input section, a display section, and a communication section (all not shown).

The console 101 allows an image based on image data having been transmitted from the radiographic image detection device 2 to be displayed and allows the image data to be subjected to various types of image processing In the present embodiment, the console 101 is configured to connect to external devices such as an HIS/RIS 121, a PACS server 122, and an imager 123 via network N.

Next, the operation of the radiographic image detection device 2 in the present embodiment will be described.

When the radiographic image detection device 2 is placed in a cradle 4, then the connection detection-determination section 43 of the cradle 4 side detects/determines that the detection device side connector section 26 has been connected to the output connector section 42 of the cradle 4 and then the switch 44 is turned on. Then, via the output connector section 42, from an external power supply, electric power having for example, a voltage of 3.6 V and a current value of 10 A is fed to the detection device side connector section 42.

The connection detection section of the radiographic image detection device 2 side detects the voltage of electric power fed to the detection device side connector section 26 to output an Lo signal from the first comparator 61*a* and an Hi signal from the second comparator 61*b*. The determination circuit 62 judges that low-voltage power, i.e., electric power from the cradle 4 has been fed based on the signals from the first comparator 61*a* and the second comparator 61*b* to allow the first switch 63*a* to remain OFF and only the second switch 63*b* to be ON.

Thereby, low-voltage and high-current power from the cradle 4 is fed to the battery 28 via the power receiving circuit 29.

When the power feeding cable 52 is connected to the detection device side connector 26 of the radiographic image detection device 2, the connection detection-determination section of the power feeding cable 52 side detects/determines that the power feeding cable 52 has been connected to the detection device side connector 26 and then an unshown switch is turned on. Then, via the power feeding cable 52, from the external power supply, electric power of for example, a voltage of 15 V and a current value of 3 A is fed to the detection devise side connector section 26.

The electric power feeding section determination section 60 of the radiographic image detection device 2 side detects the voltage of electric power fed to the detection device side connector section 26 to output Hi signals from the first comparator 61*a* and the second comparator 61*b*. The determination circuit 62 judges that based on the signals from the first comparator 61*a* and the second comparator 61*b*, high-voltage power, i.e., electric power via the power feeding cable 52 has been fed to allow the first switch 63*a* to be ON and the second switch 63*b* to be OFF.

Thereby, high-voltage and low-current power from the power feeding cable 52 is sent to the charging circuit 6 to be converted into electric power having a voltage (for example, 3.6 V) and a current value (for example, 3 A) suitable for charging the battery 28 in the charging circuit 6.

Further, in this case, electric power is fed to each functional section of the radiographic image detection device 2 from the battery 28 or an external power supply via the detection device side connector section 26. In parallel with charging of the battery 28, image capturing and data processing can be carried out. Herein, when image capturing is performed with charging, a fed current value is increased corresponding to a portion of electric power also fed to each functional section concurrently.

On the other hand, when neither the output connector section 42 nor the power feeding cable 52 is connected to the detection device side connector section 26 of the radiographic image detection device 2, Lo signals are output to the determination circuit 62 from both the first comparator 61*a* and the second comparator 61*b*. The determination circuit 62 judges that based on the signals from the first comparator 61*a* and the second comparator 61*b*, electric power of at least a predetermined value is not being fed to the detection device side connector section 26 to allow both the first switch 63*a* and the second switch 63*b* to be OFF. Thereby, the battery 28 and the detection device side connector section 26 are blocked to prevent the electric power of the battery 28 from flowing out to the outside from the detection device side connector section 26.

As described above, according to the present embodiment, 2 types of charging path 65 are provided and then, based on the judgment that the output connector section 42 has been connected to the detection device side connector section 26 or the power feeding cable 52 has been connected thereto, the charging path 65 can be switched. Thereby, when the output connector section 42 has been connected to the detection device side connector section 26, quick charging can be carried out with high current, and also when the power feeding cable 52 has been connected, with charging with low current, processing such as image capturing can be performed.

And, when the power feeding cable 52 has been connected, charging current is allowed to be reduced, whereby the current capacity of the power feeding cable 52 can be reduced and then the diameter of the power feeding cable 52 can also be reduced. Thereby, the manageability of the radiographic image detection device 2 is increased and then, with charging of the battery 28, image capturing can be easily carried out with no attention to the remaining level of the battery 28.

Further, since current flowing in the power feeding cable 52 is allowed to decrease, the power loss corresponding to the voltage decrease caused by the power feeding cable 52 can be reduced.

Further, when the power feeding cable 52 has been connected, charging is carried out with low current, and thereby heat generation in the charging circuit 6 is reduced and then image quality degradation due to the influence of heat can be inhibited. Still further, since the produced amount of noise from the charging circuit 6 can be inhibited, the adverse effect on image quality due to charging can be inhibited.

Furthermore, when the output connector section 42 of the cradle 4 has been connected to the detection device side connector section 26, image capturing with this state cannot be assumed, and thereby no adverse effect due to heat generation and noise production via charging needs to be taken into consideration. Therefore, in such a state, charging is carried out with high current, resulting in realization of charging for a short period of time.

Incidentally, in the present embodiment, the case that the dual-purpose electric power feeding section is the electric power feeding section 5 and the charging-dedicated electric power feeding section is the cradle 4 has been described. However, the dual-purpose electric power feeding section and the charging-dedicated electric power feeding section are not limited to those exemplified here.

For example, a constitution is employable in which a bucky apparatus 110 is electrically connected to an external power supply and then the buck apparatus 110 is mounted with a radiographic image detection device 2 to carry out charging. In this case, when image capturing is performed with charging in the state of mounting in the bucky apparatus 110, in the same manner as in the case where the power feeding cable 52 has been connected, high-voltage and low-current power is fed from the external power supply, and on the radiographic image detection device 2 side, the first charging path 65a is selected for power conversion in the charging path 6 to charge the battery 28. Further, after clinic hours such as during nighttime, the bucky apparatus 110 may be used as a charging-dedicated electric power feeding section. In this case, in the same manner as in the case where the cradle 4 has been connected, low-voltage and high-current power is fed from the external power supply, and on the radiographic image detection device 2 side, the second charging path 65b is selected and then high current is directly fed to the battery 28 without power conversion to charge the battery 28.

Further, in the present embodiment, the case that the low-current electric power feeding section is the electric power feeding section 5 as the dual-purpose electric power feeding section and the high-current electric power feeding section is the cradle 4 as the charging-dedicated electric power feeding section has been described. However, the low-current electric power feeding section and the high-current electric power feeding section are not limited to those exemplified here.

For example, in the case where as described above, the constitution that the bucky apparatus 110 is electrically connected to an external power supply and the bucky apparatus 110 is mounted with a radiographic image detection device 2 to carry out charging is employed, when even image capturing is also performed with charging in the state of mounting in the bucky apparatus 110, the drive of each functional section for image capturing and quick charging of the battery 28 may be concurrently carried out, while high current is fed. In this case, the bucky apparatus 110 functions as the high-current electric power feeding section and low-voltage and high-current power is fed from the external supply, and on the radiographic image detection device 2 side, the second charging path 65b is selected and then high current is directly fed to the battery 28 without power conversion to charge the battery 28.

As in the case where a radiographic image detection device 2 is used by being mounted in the bucky apparatus 110, when the radiographic image detection device 2 is connected to the external power supply at a shortest distance for charging and image capturing, differently from connection using a power feeding cable 52, inductance is reduced and current loss is also reduced even if high current is fed, and thereby, with quick charging of the batter 28 with high current, each functional section for image capturing can be driven.

Further, in the present embodiment, the power feeding cable 52 may be configured to double as a communication cable, or a constitution is employable in which the cradle 4 is provided with a communication terminal to perform both charging of the battery 28 and communications.

In addition, it goes without saying that the present invention is not limited to the above embodiment and can be appropriately converted

What is claimed is:

1. A radiographic image capturing system having,
a low-current electric power feeding section to feed low-current electric power,
a high-current electric power feeding section to feed high-current electric power, and
a cassette-type radiographic image detection device in which a battery to feed electric power to each functional section is incorporated in a housing so as to drive the each functional section by feeding electric power from the battery,
the radiographic image detection device comprising:
a power receiving side connection section which is configured to be electrically connectable to the low-current electric power feeding section and the high-current electric power feeding section to receive electric power from an electric power feeding section having been connected,
a first charging path in which a power conversion section to convert electric power fed from the electric power feeding section into charging electric power is provided and electric power fed from the electric power feeding section is fed to the battery after converted into charging electric power by the power conversion section,
a second charging path in which electric power fed from the electric power feeding section is fed to the battery without conversion,
an electric power feeding section determination section to determine whether an electric power feeding section currently connected to the power receiving side connection section is the low-current electric power feeding section or the high-current electric power feeding section, and
a charging path switching section in which the first charging path and the second charging path are switched so that when the electric power feeding section determination section has determined that the low-current electric power feeding section has been connected to the power receiving side connection section, electric power is fed via the first charging path and when the electric power feeding section determination section has determined that the high-current electric power feeding section has been connected to the power receiving side connection section, electric power is fed via the second charging path.

2. The radiographic image capturing system of claim 1, wherein the low-current electric power feeding section further comprises a power feeding cable and connects with the power receiving side connection section via the power feeding cable; and
the high-current electric power feeding section comprises a cradle connection terminal and connects with the power receiving side connection section via the cradle connection terminal.

3. The radiographic image capturing system of claim 1, wherein the low-current electric power feeding section is a dual-purpose electric power feeding section to concurrently drive each functional section and charge the battery.

4. The radiographic image capturing system of 1, wherein the high-current electric power feeding section is a dedicated electric power feeding section to charge specifically for charging the battery.

5. The radiographic image capturing system of 1, wherein the battery is lithium-ion capacitor.

6. A radiographic image detection device of a cassette-type incorporating a battery to feed electric power to each functional section in a housing so as to drive the each functional section by feeding electric power from the battery, the radiographic image detection device comprising:

a power receiving side connection section which is configured to be electrically connectable to an external low-current electric power feeding section to feed low-current electric power and an external high-current electric power feeding section to feed high-current electric power so as to receive electric power from an outside, a first charging path in which a power conversion section to convert electric power fed from an outside into charging electric power is provided and electric power fed from the outside is fed to the battery after converted into charging electric power by the power conversion section, a second charging path in which electric power fed from the outside is fed to the battery without conversion, an electric power feeding section determination section to determine whether an electric power feeding section connected to the power receiving side connection section is the low-current electric power feeding section or the high-current electric power feeding section, and a charging path switching section in which the first charging path and the second charging path are switched so that when the electric power feeding section determination section has determined that the low-current electric power feeding section has been connected to the power receiving side connection section, electric power is fed via the first charging path and when the electric power feeding section determination section has determined that the high-current electric power feeding section has been connected to the power receiving side connection section, electric power is fed via the second charging path.

7. The radiographic image detection device of claim 6, wherein the low-current electric power feeding section is used as a dual-purpose electric power feeding section to concurrently drive each functional section and charge the battery when determined that the low-current electric power feeding section has been connected.

8. The radiographic image detection device of claim 6, wherein the high-current electric power feeding section is used as a charging-dedicated electric power feeding section dedicated to charging the battery when determined that the high-current electric power feeding section has been connected.

9. The radiographic image detection device of 6, wherein the battery is lithium-ion capacitor.

* * * * *